(12) United States Patent
Ellefson et al.

(10) Patent No.: US 9,814,630 B2
(45) Date of Patent: Nov. 14, 2017

(54) VAGINAL INSERT DEVICE HAVING A SUPPORT PORTION WITH PLURALITY OF FOLDABLE AREAS

(75) Inventors: Kimberly Louise Ellefson, Oshkosh, WI (US); Jason Robert Boon, Appleton, WI (US); Garry Roland Woltman, Appleton, WI (US); MaryAnn Zunker, Oshkosh, WI (US); Patricia Ann Samolinski, Winneconne, WI (US); Walter George Bauer, Neenah, WI (US); Vivian Kate Barad, San Francisco, CA (US); Nicole Sarah Kahn, San Francisco, CA (US); Gina Lynn Romero, Los Altos, CA (US); Elger Oberwelz, San Francisco, CA (US); James Rolfe Yurchenco, Palo Alto, CA (US); Jonah Lawrence Houston, San Jose, CA (US); Tiffany Heather Card, Los Altos Hills, CA (US); Martin Schnitzer, San Francisco, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1812 days.

(21) Appl. No.: 12/977,561

(22) Filed: Dec. 23, 2010

(65) Prior Publication Data

US 2012/0165599 A1 Jun. 28, 2012

(51) Int. Cl.
*A61F 2/00* (2006.01)
*A61F 13/34* (2006.01)
(Continued)

(52) U.S. Cl.
CPC ............ *A61F 13/34* (2013.01); *A61F 13/202* (2013.01); *A61F 13/2022* (2013.01); *A61F 13/2088* (2013.01); *A61F 13/26* (2013.01)

(58) Field of Classification Search
CPC ........... A61B 2017/00805; A61B 17/42; A61F 2/0045; A61F 2/005; A61F 2/0036;
(Continued)

(56) References Cited

U.S. PATENT DOCUMENTS

| 4,212,301 A | 7/1980 | Johnson |
| 5,036,867 A | 8/1991 | Biswas |

(Continued)

FOREIGN PATENT DOCUMENTS

| EP | 1 481 656 A1 | 12/2004 |
| GB | 0 113 275 A | 10/1918 |

(Continued)

OTHER PUBLICATIONS

U.S. Appl. No. 12/977,547, filed Dec. 23, 2010, by Ellefson et al. for "Vaginal Insert Device Having a Support Portion with Plurality of Struts."

*Primary Examiner* — Navin Natnithithadha
*Assistant Examiner* — Sunita Reddy
(74) *Attorney, Agent, or Firm* — Kimberly-Clark Worldwide, Inc.

(57) ABSTRACT

Generally, a vaginal insert device used to treat urinary incontinence is disclosed. The vaginal insert device includes a support portion, a stabilizing portion, a removal device, and at least one fluid passageway extending though the support portion. The substantially cylindrical support portion has a distal end and a proximal end. In addition, the support portion has a plurality of foldable areas extending from the distal end to the proximal end. Desirably, the plurality of foldable areas helically curve as the plurality of foldable areas extend from the distal end to the proximal end. The largest outer circumference of the support portion has an insertion diameter when the plurality of foldable areas are compressed and foldable inward and an in-use (Continued)

diameter wherein the plurality of foldable areas are extended outward into a maximum in-use diameter position. Desirably, the in-use diameter is larger than the insertion diameter.

14 Claims, 5 Drawing Sheets

(51) Int. Cl.
*A61F 13/26* (2006.01)
*A61F 13/20* (2006.01)

(58) Field of Classification Search
CPC .......... A61F 2/0009; A61F 2/042; A61F 6/08; A61F 2250/0007; A61F 5/48; A61F 2/0022; A61F 2/0063; A61F 13/26; A61F 2002/047; A61F 2210/009; A61F 2250/0039; A61F 2/004; A61F 2/04; A61F 6/12; A61F 13/2051; A61F 2210/0033; A61F 2220/0016; A61F 2230/001; A61F 2250/0003; A61F 2250/001; A61F 2250/18; A61F 2250/0067; A61F 2250/0087; A61F 2250/0097; A61F 2/0027; A61F 2/0031; A61F 13/20; A61F 13/202; A61F 13/2025; A61F 13/2034; A61F 13/2071; A61F 13/34; A61F 2002/0068; A61F 2002/0072; A61F 2002/009; A61F 2002/0852; A61F 2002/0888; A61F 2002/3055; A61F 2002/9517; A61F 2210/0042; A61F 2210/0057; A61F 2210/0061; A61F 2210/008; A61F 2220/0008; A61F 2240/002; A61F 2250/0001; A61F 2250/0002; A61F 2250/0008; A61F 2250/00; A61F 2250/0068; A61F 2250/0071; A61F 2250/0078; A61F 2/0077; A61F 2/0095; A61F 2/0805; A61F 2/0811; A61F 2/962

USPC ........................................ 600/29, 20; 29/428
See application file for complete search history.

(56) References Cited

U.S. PATENT DOCUMENTS

| | | | |
|---|---|---|---|
| 5,386,836 | A | 2/1995 | Biswas |
| 5,483,976 | A | 1/1996 | McLaughlin et al. |
| 5,618,256 | A | 4/1997 | Reimer |
| 5,718,675 | A | 2/1998 | Leijd |
| 6,090,038 | A | 7/2000 | Zunker et al. |
| 6,142,928 | A | 11/2000 | Zunker et al. |
| 6,458,072 | B1 | 10/2002 | Zunker |
| 6,676,594 | B1 | 1/2004 | Zunker et al. |
| 6,679,831 | B1 | 1/2004 | Zunker et al. |
| 6,739,340 | B1 | 5/2004 | Jensen et al. |
| 6,770,025 | B2 * | 8/2004 | Zunker .......................... 600/29 |
| 6,969,380 | B1 | 11/2005 | Zunker |
| 2003/0149334 | A1 | 8/2003 | Ulmsten et al. |
| 2004/0122285 | A1 | 6/2004 | Zunker |
| 2004/0158122 | A1 | 8/2004 | Guerquin |
| 2005/0148995 | A1 | 7/2005 | Shepard et al. |
| 2006/0167428 | A1 | 7/2006 | Denti et al. |
| 2006/0167430 | A1 | 7/2006 | Denti et al. |
| 2007/0203429 | A1 | 8/2007 | Ziv |
| 2007/0244352 | A1 | 10/2007 | Ziv |
| 2008/0009662 | A1 | 1/2008 | Bartning et al. |
| 2008/0009663 | A1 | 1/2008 | Bartning et al. |
| 2008/0009664 | A1 | 1/2008 | Bartning et al. |
| 2008/0009666 | A1 | 1/2008 | Bartning et al. |
| 2008/0009814 | A1 | 1/2008 | Bartning et al. |
| 2008/0033230 | A1 | 2/2008 | Bartning et al. |
| 2008/0033231 | A1 | 2/2008 | Bartning et al. |
| 2008/0108861 | A1 | 5/2008 | Harris et al. |
| 2008/0149109 | A1 | 6/2008 | Ziv |
| 2008/0228027 | A1 | 9/2008 | Guerquin et al. |
| 2008/0281149 | A1 | 11/2008 | Sinai et al. |
| 2009/0203959 | A1 | 8/2009 | Ziv et al. |
| 2009/0247929 | A1 * | 10/2009 | Hou et al. ....................... 604/15 |
| 2010/0217068 | A1 | 8/2010 | Ziv et al. |

FOREIGN PATENT DOCUMENTS

| | | |
|---|---|---|
| GB | 2 073 592 | 10/1981 |
| KR | 10-2002-0015681 A | 2/2002 |
| WO | WO 1999/032061 A1 | 7/1999 |
| WO | WO 2002/078586 A2 | 10/2002 |
| WO | WO 2005/041833 A1 | 5/2005 |
| WO | WO 2005/112862 A1 | 12/2005 |
| WO | WO 2011/080628 A2 | 7/2011 |

* cited by examiner

VAGINAL INSERT DEVICE HAVING A SUPPORT PORTION WITH PLURALITY OF FOLDABLE AREAS

BACKGROUND

Female stress urinary incontinence, the involuntary loss of urine, may occur during normal movements and everyday activities including laughing, coughing, sneezing, exercise and any physical activity that causes an increase in intra-abdominal pressure resulting in urine to flow from the bladder through the urethral tube to the outside of the body. The primary causative factor resulting in genuine stress incontinence is the incomplete transmission of abdominal pressure to the proximal urethra due to the displacement of the urethra from its intra-abdominal position. Stress incontinence is related to weakened pelvic floor muscles tissue and ligaments that are no longer able to adequately support the proximal urethra and elevate it above the pelvic floor thereby subjecting it to increases in intra-abdominal pressure, thus allowing compression and maintenance of continence [Urogynecology and Urodynamics—Theory and Practice, chapter 36, page 494]. Stress incontinence may result from repetitive straining of the pelvic muscles, pregnancy, obesity etc. that lead to a loss of pelvic muscle tone and other medical causes that can also occur naturally with the aging process. Some women, especially women who have given birth to one or more children, and older women, can experience incidences of involuntary urine loss due to stress urinary incontinence or combined stress and urge incontinence.

As the world's female population ages, there is an ever-increasing need for a consumer friendly, method or measure to reduce the involuntary urine loss commonly associated with stress urinary incontinence. Although there are specialized products available for this purpose, many can only be purchased with a prescription and they need to be properly sized, physically inserted and/or adjusted by a medical practitioner for them to perform correctly. Over the counter solutions like feminine pads and incontinence pads being bulky and exterior to the body are not discreet and do not mitigate the problem before absorbent protection is required.

In view of the lack of commercially available devices that are easy to use, there is a need for a urinary incontinence device that can be purchased by the consumer and that is uncomplicated and user friendly. Furthermore, there is a need for a urinary incontinence device that is easy for a woman to insert into and remove from her body that is comfortable to wear and provides both physical and psychological assurance that it is capable of properly performing over an extended period of time.

SUMMARY

Generally, a vaginal insert device used to treat urinary incontinence is disclosed. The vaginal insert device includes a support portion, a stabilizing portion, a removal device, and at least one fluid passageway extending though the support portion. The vaginal insert expands in the vagina to deliver an outward compression force against the bladder neck via the anterior vaginal wall to assist in the prevention of urinary stress incontinence.

The substantially cylindrical support portion has a distal end and a proximal end. In addition, the support portion has a plurality of foldable areas that extend from the distal end to the proximal end.

The largest outer circumference of the support portion has an insertion diameter when the plurality of foldable areas are compressed and folded inward and an in-use diameter wherein the plurality of foldable areas are extended outward into a maximum in-use diameter position. Desirably, the in-use diameter is larger than the insertion diameter. For example, the in-use diameter of the support portion may range from about 20 to about 60 mm and the insertion diameter of the support portion may range from 10 to about 25 mm.

In an exemplary embodiment, the stabilizing portion is attached to the distal end of the support portion. The stabilizing portion provides a means to prevent the vaginal insert device from unintentionally moving, thereby stabilizing the vaginal insert device within the vaginal cavity.

In an exemplary embodiment, at least one fluid passageway extends between the plurality of foldable areas.

In another embodiment, a removal member may be attached to the vaginal insert device. The removal member may be anything known by one skilled in the art to allow a user to remove the vaginal insert device.

The support portion of the vaginal insert device has three separate configurations or modes depending on whether the device is being inserted, is in-use or being removed. Accordingly, the support portion has an insertion mode, an in-use mode, and a removal mode. The insertion mode may include the plurality of foldable areas being compressed and folded inward so that the largest outer circumference of the support portion has an insertion diameter.

After insertion of the vaginal insert into the vaginal cavity, the plurality of foldable areas expand to a maximum conical shape to transition between the insertion mode and the in-use mode wherein the largest outer circumference of the support portion has an in-use diameter larger than the insertion diameter. Desirably, the largest outer circumference in the in-use mode is at the distal end of the support portion.

Desirably, the vaginal insert device may be stored in the insertion mode within an applicator. The applicator maintains the support portion of the vaginal insert device in the insertion mode, and removal of the vaginal insert device from the applicator transitions the support portion from the insertion mode to the in-use mode.

In exemplary embodiments, when the vaginal insert device is in the removal mode, the largest outer circumference of the support portion has a removal diameter that is the same size as the in-use diameter. In other embodiments, the support portion becomes elongated when the removal member is activated so that the largest outer circumference of the support portion has a removal diameter smaller than the in-use diameter. Desirably, the removal member comprises a string, and tension on the string compels the support portion to an elongated position in transition between the in-use mode and the removal mode.

Desirably, the vaginal insert device is constructed of a compliable resilient material.

In another embodiment, the vaginal insert device includes an absorbent material coupled to the vaginal insert device. In this embodiment, the vaginal insert device acts as both a urinary incontinence device and a tampon.

In another embodiment, an apparatus with the vaginal insert device and an applicator coupled to the vaginal insert device for facilitating insertion of the vaginal insert device is disclosed.

In another embodiment, a method of manufacturing a vaginal insert device including providing a vaginal insert device as described above, compressing the plurality of foldable areas inward wherein the largest outer circumference of the support portion has an insertion diameter and storing the vaginal insert device within an applicator.

In another embodiment, a kit is disclosed having at least a first vaginal insert device as described above and a second vaginal insert device as described above. In this embodiment, the first vaginal insert device comprises a first length and a first in-use diameter and the second vaginal insert device comprises a second length and a second in-use diameter. The second length may be different from the first length, and/or the first in-use diameter may be different from the second in-use diameter. This enables a new user to use different sized vaginal insert devices and determine the proper size for continued use.

BRIEF DESCRIPTION

FIG. 1 is a mid-sagittal section of a human torso showing one embodiment of a vaginal insert device positioned in the vaginal canal showing the support portion of the vaginal insert device aligned with the bladder neck region to cooperate with the symphysis pubis to allow the urethral tube to be compressed upon itself and alleviate urinary incontinence during episodes of increased intra-abdominal pressure.

DETAILED DESCRIPTION

Generally, a vaginal insert device used to treat urinary incontinence is disclosed. The vaginal insert device includes a support portion, a stabilizing portion, a removal device, and at least one fluid passageway extending though the support portion.

Figure 1:
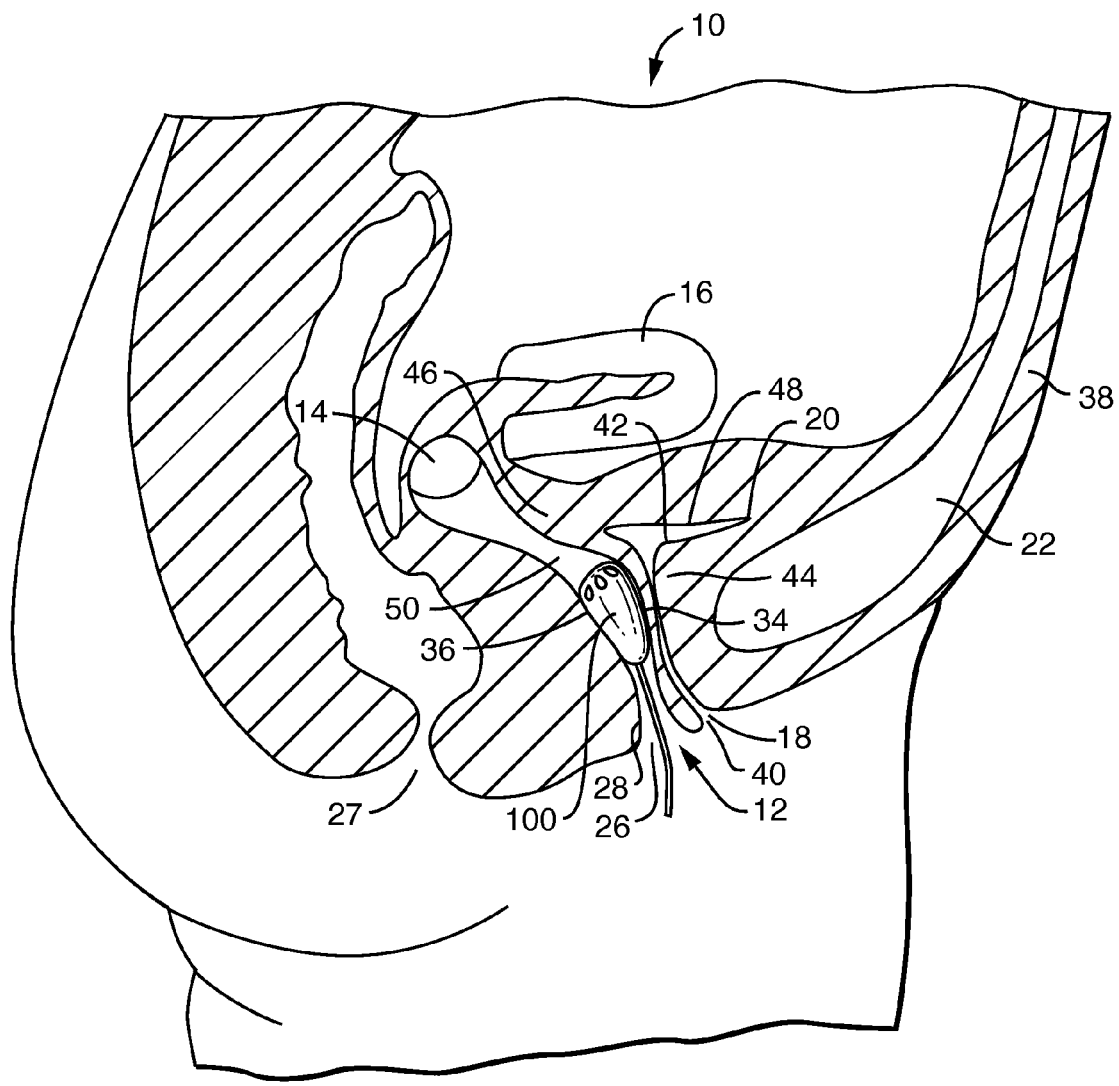

Turning now to FIG. 1, a human torso 10 of a female is shown with a vagina 12, a cervix 14, a uterus 16, a urethra 18, a bladder 20 and a symphysis pubis 22. The vagina 12 has an introital opening 24 that exits the human body 10 and contains a vaginal canal 26 that extends from the introital opening 24 to the cervix 14. The vaginal canal 26 has a length that ranges from between about 4 inches to about 6 inches (about 102 to about 153 mm) in most women. The cervix 14 is the entrance to the womb and is located between the upper aspect of the vaginal canal 26 and the uterus 16. The rectum 27 is located posterior to the vagina 12. The vaginal canal 26 has an inner periphery 28.

The inner periphery 28 is made up of a right lateral wall, a left lateral wall, an anterior wall 34, and a posterior wall 36. The four walls encompass the entire 360 degrees of the inner periphery 28. The anterior wall 34 is located closest to the urethra 18 and the urethra 18 is located between the symphysis pubis 22 and the vagina 12.

The vaginal canal 26 can be divided into three approximately equal sections, each representing about one-third of the overall length. Each section is approximately 2 inches (approximately 51 mm) in length. The middle third of the vaginal canal 26 is the most important section for alleviating female urinary incontinence because of its proximity to the urethra 18 and is the location where a vaginal insert device should be positioned. The middle third of the vaginal canal 26 is also horizontally offset from the symphysis pubis 22, which is a bony prominence situated adjacent to a front portion 38 of the human torso 10 and may be referred to as the bladder neck region 50. Cooperation between a vaginal insert device positioned in the vagina 12 and the symphysis pubis 22 allows the urethra 18 to be compressed upon itself thereby providing a means to alleviate involuntary urine flow from the bladder.

The urethra 18, also referred to as a urethral tube, is a hollow tubular structure that extends from a first opening 40 that exits the human body 10 to a second opening 42 situated at the lower surface of the bladder 20. The urethra 18 has a length of about 1.5 inches (about 38 mm) in most women. The urethra functions to discharge urine, which is temporarily stored in the bladder 20, from the human body. The urethra 18 has a plurality of urethral sphincter muscles 44 located along the length of its inner periphery. The urethral sphincter muscles 44 are situated below the opening 42 and are ring like muscles that normally maintain constriction of the urethra 18 to prevent the passage of urine. The relaxation of the urethral sphincter muscles 44 by normal physiological functioning will permit urine to be voluntarily expelled from the body.

Again, referring to FIG. 1, the human torso 10 further includes musculature and body tissue located in the urethrovaginal myofascial area 46 that is situated between the vagina 12 and the symphysis pubis 22. The bladder 20 lies posterior to the symphysis pubis 22 and is separated from the rectum 27 by the vagina 12 and the uterus 16. The ureters (not shown) which transport urine from the kidneys to the bladder 20, pass from the pelvis to the posterior aspect of the urinary bladder 20. The fundus vesicae 48, into which both of the ureters terminate, is located adjacent to the anterior wall 34 of the vagina 12.

A vaginal insert device 100 is shown positioned in the vaginal canal 26 and, in particular, in the bladder neck region 50. The vaginal insert device 100 is designed to bridge across the vagina to support the musculature and body tissue located in the urethra-vaginal myofascial area 46. In other words, the vaginal insert device 100 and, in particular, the support portion 102 supports the bladder neck 50 to a more normal retropubic position thereby restoring continence.

The vaginal insert device 100 is shown in use. A portion of the vaginal insert device 100 and, in particular, the support portion 102 of the vaginal insert device 100 is directly touching the anterior and posterior walls 34 and 36. Alternatively, the insert 102 can be selectively positioned such that a portion of the top 110 can be touching both the right and left lateral walls (not shown) and the anterior and posterior walls 34, 36 to provide a supportive backdrop for the urethral tube 18 and to support the bladder neck region 50 thereby restoring continence. The urethral tube 18 will now be sufficiently compressed to intercept the flow of urine and to provide support to the urinary sphincter muscle 44 so that it can function properly. By permitting the urethral tube 18 to be compressed upon itself between the vaginal insert device 100 and the symphysis pubis 22, the involuntary flow of urine from the bladder is limited.

Referring now to FIGS. 2-9, the vaginal insert device 100 includes a generally cylindrical support portion 102, a stabilizing portion 104, a removal device 160, and at least one fluid passageway 140 extending though the support portion 102.

The support portion 102 provides for generating urethral support and has a distal end 110 and a proximal end 112. As used in the specification and claims, the distal end 110 refers to that portion of the vaginal insert device 100 that is first inserted into the vagina. The support portion 102 of the vaginal insert device 100 has three separate configurations or modes depending on whether the device is being inserted, is in-use or being removed. Accordingly, the support portion 102 has an insertion mode 202, an in-use mode 204, and a removal mode 206.

In the in-use mode, the support portion 102 has a generally conical shape. The generally conical shape may have a variety of cross-sectional shapes spanning from a five-point flower shaped cross-section, circular cross-section configuration to more of an oval cross-section configuration to more of a square cross-sectional configuration to more of a rectangular cross-sectional configuration. If the support portion has a non-round cross section, the outer circumference of the support portion 102 can be defined by connecting the outermost points of the cross-sectional area. Typically, the outer circumference of the support portion 102 has a substantially round cross-section.

Figure 2:
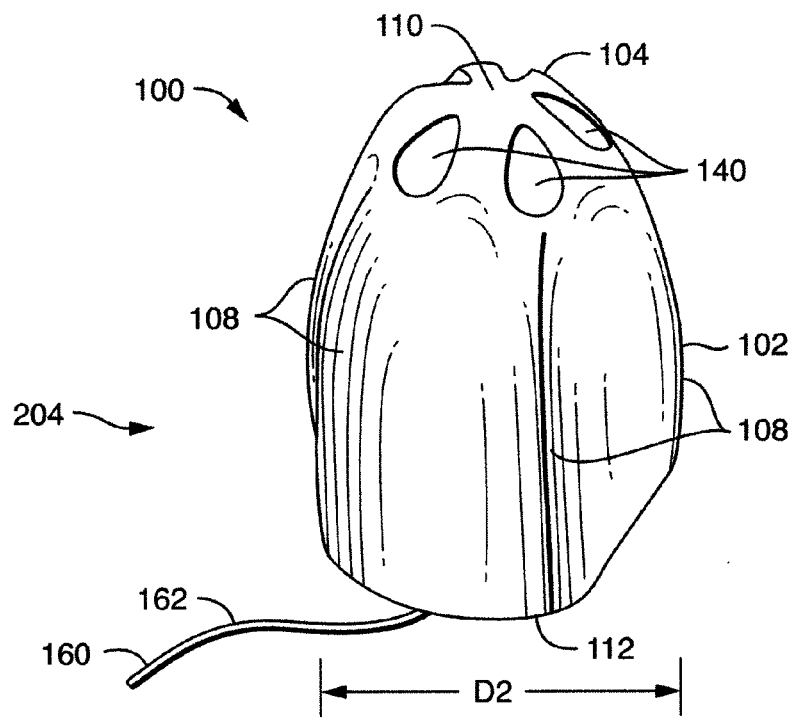
FIG. 2 is a perspective view of one embodiment of the vaginal insert device in the in-use mode.
Figure 3:
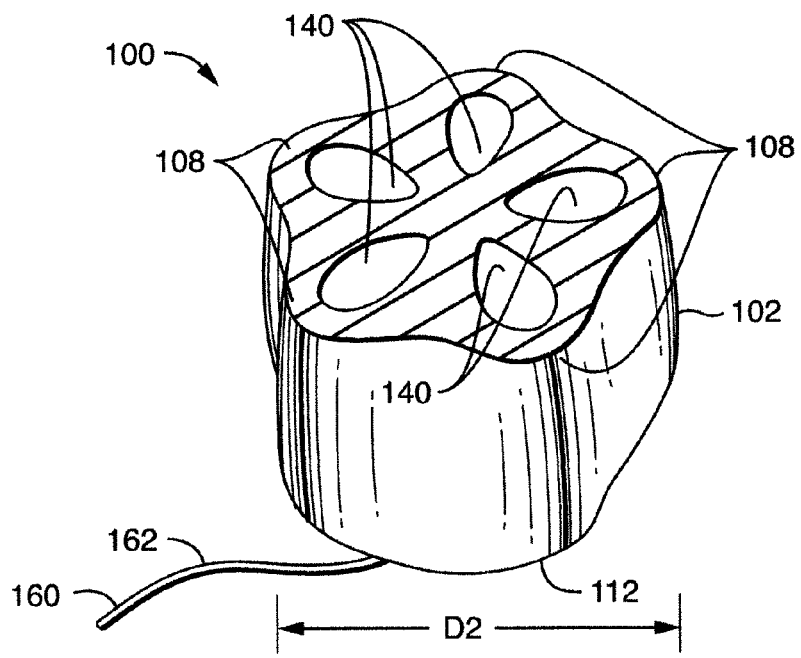
FIG. 3 is a cross-sectional view of the embodiment of FIG. 2.
Figure 4:
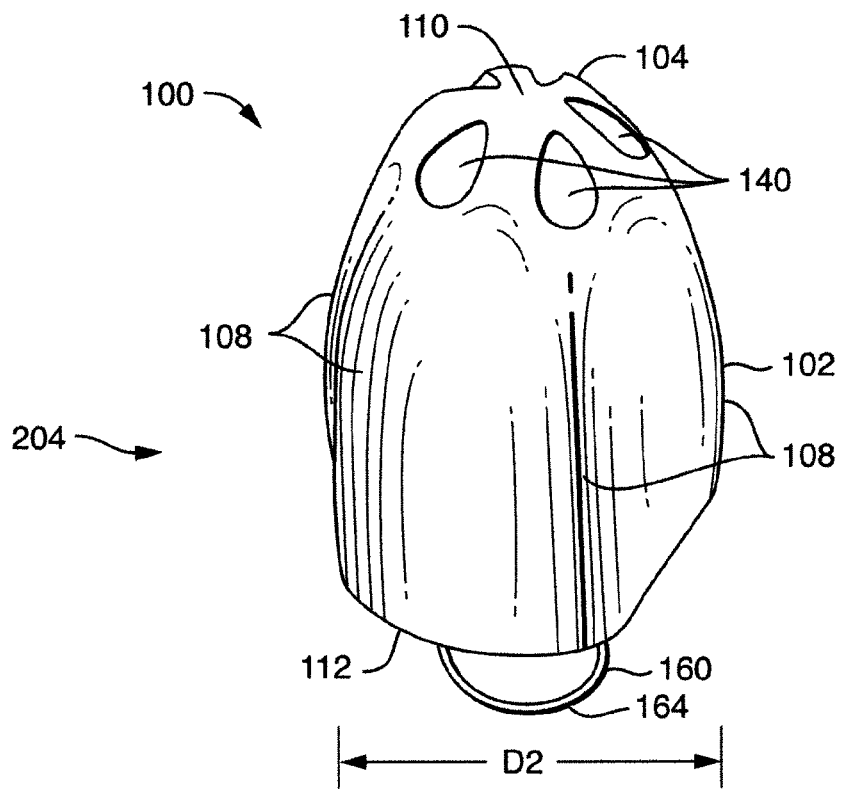
FIG. 4 is a perspective view of another embodiment of the vaginal insert device in the in-use mode.

In the in-use mode as depicted in FIGS. 2-4, the support portion 102 with a distal end 110 and a proximal end 112 expands from the insertion mode 202 to provide a conical shape as the vaginal insert device 100 is inserted into the vaginal cavity. While the support portion 102 is described as being conically shaped, it may also be shaped in the form of a pear, a tear drop, an obconical, or similar shape. Accordingly, the term "conical shape" is meant to include a shape as depicted in FIGS. 2-4, as well as a pear shape, a tear drop shape, an obconical, or similar shape.

Each of these shapes have a distal end 110 of the insert having a cross-sectional area that is greater than the cross-sectional area of the proximal end 112 of the support portion. Typically, the proximal end of the vaginal insert device will have a largest outer circumference with an in-use diameter, D2, which is larger than any other point on the support portion 102. Desirably, the support portion has an in-use diameter, D2, ranging from about 20 to about 60 mm, preferably about 40 to about 60 mm, or more preferably about 50 mm.

In addition, it is preferred that the shape of the vaginal insert device 100 does not present any sharp corners or surfaces but instead is shaped to present rounded or curved surfaces to minimize any discomfort during insertion, use, and removal of the vaginal insert device 100. Accordingly, the edges of both the distal end 110 and the proximal end 112 of the vaginal insert device 100 are rounded. The rounded edge of the proximal end 112 of the vaginal insert device 100 allows for easier removal.

While the vaginal insert device 100 is in the in-use mode 204, the device, not including the removal member may have a length of from about 10 to about 120 mm, desirably from about 30 to about 90 mm, and most desirably from about 50 to about 70 mm. The largest outer circumference of the device may also have a cross-sectional area from about 10 to about 70 mm, preferably from about 30 to about 60 mm.

As illustrated in the Figures, the support portion 100 includes a plurality of foldable areas 108 extending from the distal end 110 to the proximal end 112. Desirably, the number of foldable areas 108 extending from the distal end 110 to the proximal end 112 is between 2 and 6, and even more desirably between 4 and 6. FIGS. 1-8 illustrate a support portion having 5 foldable areas. In some embodiments, the plurality of foldable areas 108 extend straight down horizontally from the distal end 110 to the proximal end 112.

Figure 5:
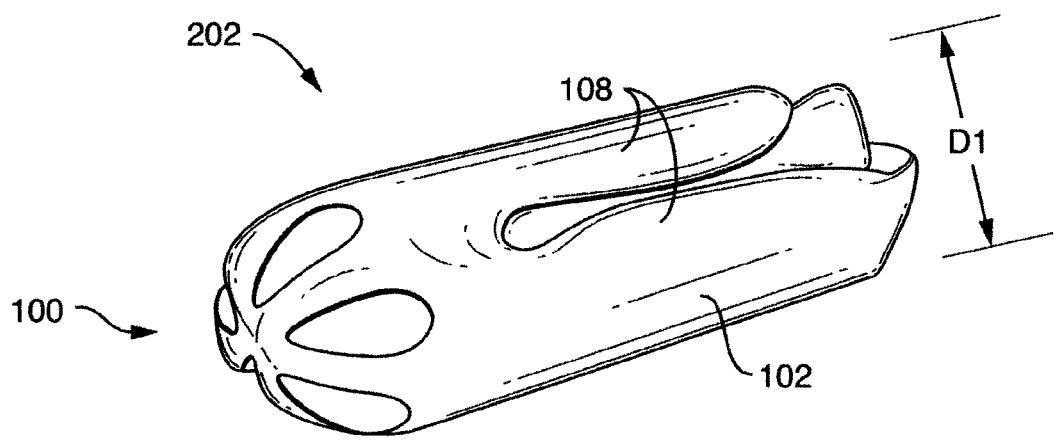
FIG. 5 is a perspective view of an embodiment of the vaginal insert device in the insertion mode.
Figure 6:
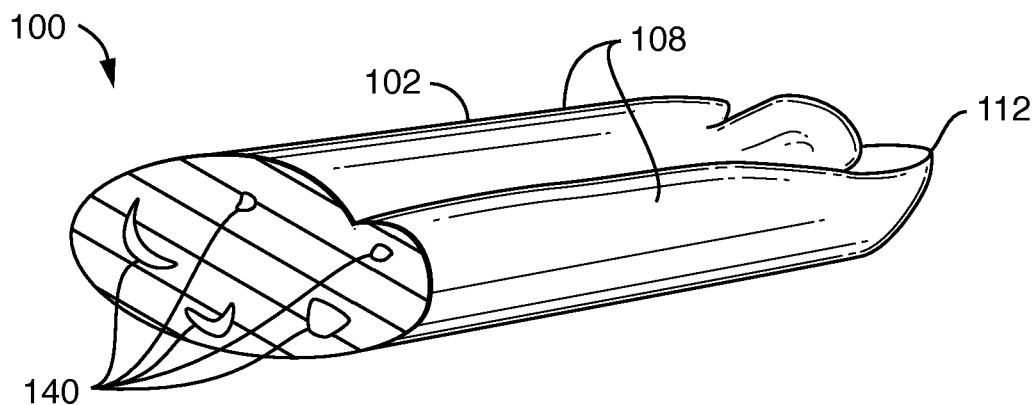
FIG. 6 is a cross-sectional view of the embodiment of FIG. 5.
Figure 7:
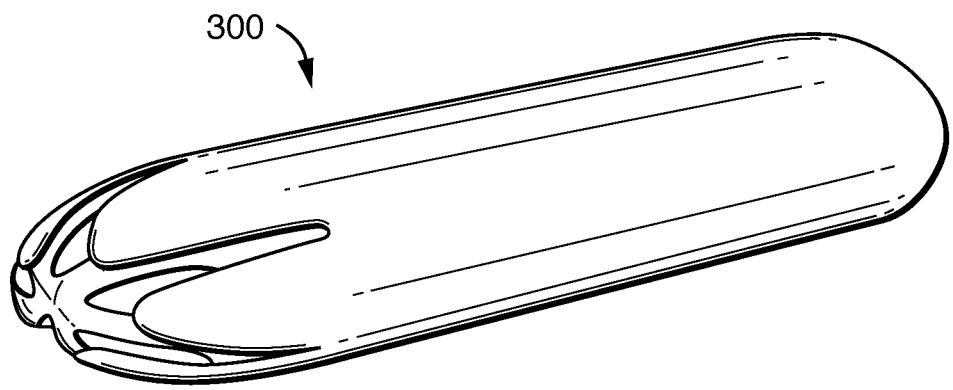
FIG. 7 is a perspective view of one embodiment of the vaginal insert device with an applicator.
Figure 8:
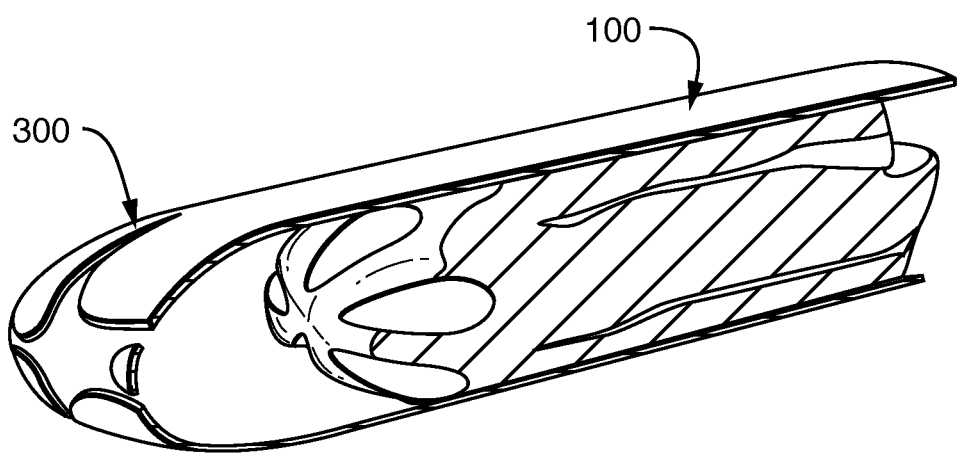
FIG. 8 is a cross-sectional view of the embodiment of FIG. 7.

FIG. 5 illustrates the vaginal insert device 100 with the support portion 102 in the insertion mode 202. When the support portion 102 is in the insertion mode 202, the plurality of foldable areas 108 are compressed or foldable inward. When the plurality of foldable areas 108 are compressed and folded inward, the largest outer circumference of the support portion 102 may have an insertion diameter, D1, which allows for easier insertion into the vagina. Typically, the distal end 110 of the support portion 102 will compress to provide a substantially cylindrical shape with a uniform diameter throughout the vaginal insert device.

Typically, to allow for easy insertion into the vagina, the insertion diameter, D1, is smaller than the in-use diameter, D2. Desirably, the support portion 102 has an insertion diameter, D1, ranging from 10 to about 25 mm, preferably about 10 to about 20 mm, or more preferably about 15 to about 20 mm. The smaller insertion diameter, D1, of the vaginal insert device 100 provides an easier way to insert the vaginal insert device 100.

The support portion 108 also includes a fluid passageway 140. The fluid passageway 140 serves two important functions. First, the fluid passageway 140 provides the space necessary in the vaginal insert device 100 to allow for the plurality of foldable areas 108 to compress inward to provide a smaller diameter when in the insertion mode 202.

Secondly, the fluid passageway 140 is provided to facilitate the natural movement of vaginal fluids entering the vaginal insert device 100. More preferably, the fluid passageway 140 is defined by the space 140 extending through the support portion 102 from the distal end 110 and terminating at the proximal end 112. Desirably, there is a fluid passageway 140 for each foldable area.

As discussed above, there is a stabilizing portion 104 attached to the distal end 110 of the support portion 102. The stabilizing portion 104 provides a means to prevent the vaginal insert device from unintentionally moving, thereby stabilizing the vaginal insert device 100 within the vaginal cavity. In an exemplary embodiment of the invention, the stabilizing portion 104 does not apply significant pressure to the wearer's vagina and/or urethra, thereby enhancing comfort. As illustrated in the Figures, a bulb or cone may be used to provide the stabilizing portion 104.

Other structure known in the art may be provided as a stabilizing portion 104 instead of a bulb to help stabilize the vaginal insert device 100 in the vagina and prevent the device from unintentionally moving. For example, at least one cone, protrusion, extension an or various shaped stents attached to the support portion could also be used as the stabilizing portion 104 to secure the vaginal insert device 100 within the vaginal cavity.

Typically, the stabilizing portion 104 may have a diameter ranging from 10 to about 25 mm, preferably about 10 to about 20 mm, or more preferably about 15 to about 20 mm.

In addition, the vaginal insert device 100 also includes a removal member 160 attached to the vaginal insert device 100. The removal member 160 may be anything known in the art to allow a user to remove the vaginal insert device 100 from the vaginal cavity. The removal member 160 may be a separate piece from the vaginal insert device 100 or may be integrally formed with the vaginal insert device 100. When the removal member 160 is attached and/or formed with the support portion 102, pulling on the removal member 160 may cause the support portion 102 to inwardly collapse upon itself to reduce the largest outer circumference of the cross-sectional area of the support portion 102 of the vaginal insert device 100 for easier removal. Preferably, the removal member 160 is connected to a portion of the proximal end 112 of the support portion 102. The removal member 160 has a shape suitable to be grasped so that the vaginal insert device 100 may be removed. For example, FIG. 4 show the removal member 160 as a ring or hook 164 and FIGS. 2-3 show the removal member 160 as a string 162.

Figure 9:
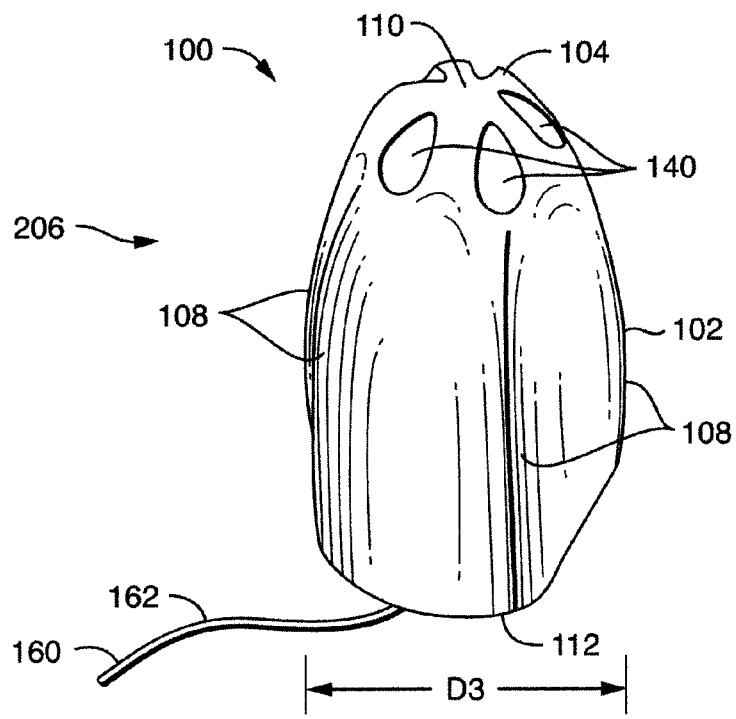
FIG. 9 is a perspective view of an embodiment of the vaginal insert device in the removal mode.

Referring to the embodiment shown in FIG. 9, the removal member 160 is shown as formed or attached within or to the support portion 102 so that as the removal member 160 is pulled downward (i.e., in a direction from the distal end 110 toward the proximal end 112 of the vaginal insert device 100), the distal end 110 of the vaginal insert device 100 is urged downward to follow the proximal end 112 of the vaginal insert device 100 out the vagina. In this embodiment, when the removal member 160 is formed within the support portion 102 and, in particular the fluid passageway 140, pulling on the removal member 160 will cause the insert 100 to inwardly collapse upon itself to reduce the cross-sectional area of the largest outer circumference area to a removal diameter, D3, to provide an exemplary removal mode 206 for the support portion 102 of the vaginal insert device 100.

In other embodiments, the removal member 160 simply acts as a way to remove the vaginal insert device 100 from the vagina. In this exemplary removal mode, the vaginal insert device 100 maintains the same shape and the same cross-sectional area so that the removal diameter, D3, is the same as the in-use diameter, D2.

The vaginal insert device 100 as described herein may be disposed after a single use, may be worn more than once, or may be reusable for a period of time (e.g., one week) before being disposed.

A method of manufacturing the vaginal insert device 100 is also disclosed. The method involves providing a vaginal insert device 100 as described herein having a substantially cylindrical support portion 102 having a distal end 110 and a proximal end 112. The support portion 102 includes a plurality of foldable areas 108 extending helically from the distal end 110 to the proximal end 112, a stabilizing portion 104 attached to the distal end 110 of the support portion 102, at least one fluid passageway 140 extending from the distal end 110 to the proximal end 112, and a removal member 160 attached to the vaginal insert device 100.

The vaginal insert device 100 is manufactured with a compliable resilient material. As used herein the specification and the claims, the term "resilient material" and variants thereof relate to materials that can be shaped into an initial shape, which initial shape can be subsequently formed into a stable second shape with mechanical deformation such as bending, compressing or twisting the material. The resilient material then substantially reverts to its initial shape when the mechanical deformation ends. The vaginal insert device described herein is formed into the in-use mode as described above. The vaginal insert device can then be mechanically deformed for insertion or storage within an applicator. After the vaginal insert device is inserted, the vaginal insert device is restored back to the in-use mode due to the ability of the resilient material to relax or spring back to its original shape. Shape memory polymers could also be used.

Advantageously, the vaginal insert device 100 may be of a unitary construction and may be formed by molding an inert, biocompatible resilient polymer. In any event, the device 100 whether made of unitary construction or otherwise, is made of a suitable biocompatible material, which is known to those of skill in the art. The device 100 may also be covered with a suitable biocompatible outer cover material. Desirably, the compliable resilient material may be formed from a closed cell polyurethane foam.

After constructed from the compliable resilient material, the vaginal insert device 100 may then be configured so that the plurality of foldable areas 108 are compressed or foldable inward so that the support portion 102 has an insertion diameter, D1. The vaginal insert device 100 can then be stored within an applicator 300.

In use, the vaginal insert device 100 is provided with the support portion 102 in the insertion mode 202. Desirably, the vaginal insert device 100 may be stored in the insertion mode 202 within an applicator 300. The applicator 300 maintains the support portion 102 of the vaginal insert device 100 in the insertion mode 202, and removal of the vaginal insert device 100 from the applicator 300 transitions the support portion 102 from the insertion mode 202 to the in-use mode 204 after insertion into the vaginal cavity. The insertion mode 202 includes the plurality of foldable areas 108 being compressed or folded inward so that the largest outer circumference of the support portion 102 has an insertion diameter, D1. Alternatively, the user of the vaginal insert device 100 may configure the vaginal insert device 100 manually by compressing the plurality of foldable areas 108 inward prior to insertion with or without an applicator.

After insertion of the vaginal insert device 100 into the vaginal cavity, the plurality of foldable areas 108 decompress and expand to a maximum in-use diameter position to transition between the insertion mode 202 and the in-use mode 204 wherein the largest outer circumference of the support portion 102 has an in-use diameter, D2, larger than the insertion diameter, D1.

When ready for removal, the user will engage the removal member 160 on the vaginal insert device 100 and remove the device from the vagina. When the vaginal insert device 100 is in the removal mode 206, the largest outer circumference of the support portion may have a removal diameter, D3, which is the same size as the in-use diameter, D2. In other embodiments, the support portion 102 may become elongated when the removal member 160 is activated so that the largest outer circumference of the support portion 102 has a removal diameter, D3, smaller than the in-use diameter, D2. Desirably, the removal member 160 comprises a string, and tension on the string compels the plurality of foldable areas 108 to an elongated position in transition between the in-use mode 204 and the removal mode 206 to facilitate easier removal.

The vaginal insert device 100 may be inserted using an applicator 300 similar to those known in the tampon art. The applicator 300 may be a push-type applicator or a retractable applicator. A collar may be added to control the depth of insertion. The applicator may be dipped in a lubricant and placed into the vagina until the base of the applicator is at the opening of the vagina.

After the user orients the applicator 300, the plunger then is pushed to its maximum extent, or until the subject feels comfortable. The plunger and barrel are then removed from the body.

The vaginal insert devices may be enclosed in a flexible bag or covered with a skin that may reduce friction during deployment, help control the device during insertion and removal, help the device to stay in place, and/or create more contact area for applying pressure to the vaginal walls. For example, the vaginal insert device may be enclosed in a vacuum shrink wrap plastic bag for insertion. Any medically appropriate materials may be used to form the bag, and depending upon the desired end-use it may be opaque, light, and/or breathable. Useful bag materials include those used in the manufacture of tampons, such as nonwoven fabrics and plastic film, including apertured films. The bag itself may also be apertured.

In exemplary embodiments, the stabilizing portion 104 may be formed integrally with the support portion 102. In other embodiments, the stabilizing portion 104 may be formed separately from the support portion 102 and attached by an attachment means, such as an adhesive. Similarly, the removal member 160 may be formed integrally with the support portion 102. In other embodiments, the removal member 160 may be formed separately from the support portion 102 and attached by an attachment means, such as an adhesive.

Figure 10:
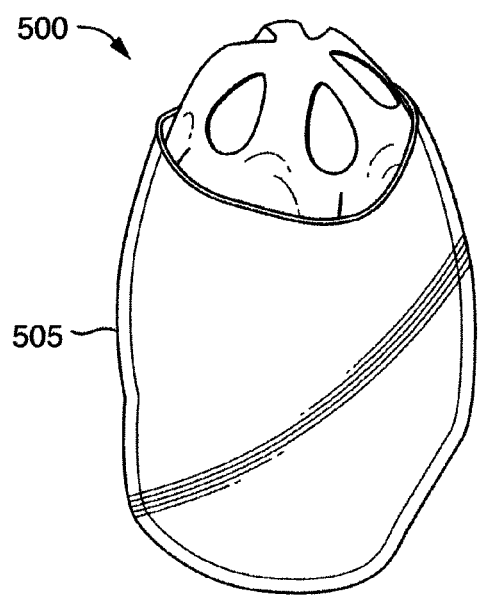
FIG. 10 is a perspective view of an alternative embodiment of the vaginal insert device including an absorbent material coupled to the device.

In another exemplary embodiment as depicted in FIG. 10, the vaginal insert device 500 may also include an absorbent material 505. The absorbent material 505 may surround the support portion of the vaginal insert device or extend from the distal end of the device. In this embodiment, the vaginal insert device may be used as both a urinary incontinence device and a tampon which can be useful for absorbing body fluid from a woman's vagina, especially during her menstrual cycle. The absorbent material 505 is attached to the vaginal insert device 500 and is designed to be inserted above the introital region of a woman's vagina and is designed to function so as to intercept the fluid flow of menses, blood, and other body fluids, and prevent the fluid from exiting the vagina. It should be noted that, while in use, the vaginal insert device 500 will be entirely positioned within the woman's vagina.

The mass of absorbent material 505 can be formed from absorbent fibers which are assembled into an absorbent sheet or ribbon. One exemplary type of sheet for practicing the invention is described in patent application PCT/EP2004/006441 titled: "Airlaid Process With Improved Throughput", filed Jun. 16, 2003, published Dec. 29, 2004 as WO2004/113608, which is owned by the same assignee as this application and is incorporated herein by reference. Alternatively, the material 505 can be formed from a general mass of absorbent fibers. In either case, the fibers are then rolled or assembled, respectively, and compressed into a generally cylindrical and elongated shape. Two processes for forming such an absorbent sheet are known as "carding" and "airlaying." Depending upon the desired absorbency one desires in the finished tampon, the basis weight of the absorbent sheet can vary. The U.S. Food and Drug Administration (FDA) has set absorbency standards for "junior", "regular", "super", "super-plus" and "super-plus-plus" size tampons. In order to meet the certain standards for these sizes, the absorbent sheets are targeted to have basis weights of about 100 grams per square meter (gsm), 120-150 gsm, 170-180 gsm, 210-230 gsm, and 240-260 gsm, respectively, and as much as 270-290 gsm. Typically, the formation process is controlled to produce an absorbent sheet with a width of between about 40 to about 60 mm, preferably about 50 mm. The basis weight and/or the length of the absorbent materials may also be adjusted to form the different size inserts.

The absorbent material 505 is a plurality of fibers which are capable of absorbing. The first type of fiber (also referred to generally herein as binder fiber) is bondable to fibers of the plurality of fibers. Additionally, the plurality of fibers may be a homogeneous mixture of the types of fibers and additionally, or alternatively, the second type of fiber may have a material composition different than the first type of fiber. For example, the bondable lint type of fibers may be polymer fibers. Material 505 includes a second type of fiber which may be cellulosic fibers such as wood pulp, cotton, rayon, viscose, LYOCELLA® which is from Lenzing Company of Austria, or mixtures of these or other cellulosic fibers. The second type fiber may be a natural type fiber and/or it may not be autogenously bondable to other like type fibers. The absorbent material can be a blend of viscose and hinder fibers. Some blends which are believed to work well include a blend of about 70% viscose to about 95% viscose with the remainder about 30% binder fiber to about 5% binder fiber; and more advantageously about 85-90% viscose and the remainder about 15-10% binder fiber. The particular blend of fibers can vary depending upon one's preference in combination with also achieving the features of the invention.

More specifically, for example, the plurality of fibers could be either synthetic fibers or natural fibers, as long as they have the desired absorbent and/or bondable characteristics. Synthetic fibers include those made from polyolefins, polyamides, polyesters, rayon, acrylics, viscose, superabsorbents, LYOCELL® regenerated cellulose and any other suitable synthetic fibers known to those skilled in the art. Many polyolefins are available for fiber production, for example polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Another fiber could be a bi-component polyester sheath and polyethylene core and known as T255 made by Trevira of Germany. Other polyolefins are also available. Suitable rayon fibers are 1.5 denier Merge 18453 fibers from Acordis Cellulose Fibers Incorporated of Axis, Ala. The fibers can be treated by conventional compositions and/or processes to enable or enhance wettability.

Natural fibers can include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Crimping may be imparted to the fibers, e.g., by conventional means. Curl may be imparted to the fibers, e.g., by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fiber which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation.

For the cellulosic fiber (e.g., viscose, rayon, etc.), the fibers should have a staple length of between about 5 to about 35 mm. The fibers should have a denier of between about 2 to about 6. Denier is a unit of fineness of yarn based on a standard of 50 milligrams (mg) for 450 meters of yarn. The fibers can have a circular, a bi-lobal, a tri-lobal cross-sectional configuration, or some other cross-sectional configuration known to those skilled in the art. The bi-lobal configuration has a cross-sectional profile which looks like a dog bone while the tri-lobal configuration has a cross-sectional profile which looks like a "Y". The fibers can also be bleached if desired.

When cotton fibers are used, the cotton fibers should have a staple length of between about 5 to about 20 mm. The cotton fibers should generally have a fiber size of between about 150 to about 280 microns. The cotton fibers can also be bleached if desired. Bleaching will make the cotton fibers whiter in appearance.

In another embodiment, there is a kit containing at least two vaginal inserts devices as described herein. In this kit, the first vaginal insert device may have a first length and a first in-use diameter and the second vaginal insert device has a second length and a second in-use diameter. The second length is different from the first length, and the first in-use diameter is different from the second in-use diameter to allow a user to determine the size of vaginal insert device to be used.

Other modifications and variations to the appended claims may be practiced by those of ordinary skill in the art, without departing from the spirit and scope as set forth in the appended claims. It is understood that features of the various examples may be interchanged in whole or part. The preceding description, given by way of example in order to enable one of ordinary skill in the art to practice the claimed invention, is not to be construed as limiting the scope of the invention, which is defined by the claims and all equivalents thereto.

We claim:

1. A vaginal insert device comprising:
   a compliable resilient material;
   a support portion having as distal end and a proximal end, the support portion having a plurality of foldable areas extending from the distal end to the proximal end, wherein a largest outer circumference of the support portion has an insertion diameter when the plurality of foldable areas are in a compressed position;
   a stabilizing portion attached to the distal end of the support portion;
   at least one tubular fluid passageway surrounded by the compliable resilient material of the vaginal insert device and extending between the distal end and the proximal end of the support portion and open at the distal end and the proximal end of the support portion; and
   a removal member attached to the vaginal insert device.

2. The vaginal insert device of claim 1 wherein the largest outer circumference of the support portion has an in-use diameter wherein the plurality of foldable areas are extended outward into a substantially conical shape, wherein the in-use diameter is larger than the insertion diameter.

3. The vaginal insert device of claim 2 wherein the in-use diameter of the support portion ranges from about 20 to about 60 mm and the insertion diameter of the support portion ranges from about 10 to about 25 mm.

4. The vaginal insert device of claim 1 wherein the plurality of foldable areas are horizontally straight as the plurality of foldable areas extend from the distal end to the proximal end, and wherein the largest outer circumference is at the distal end of the support portion.

5. The vaginal insert device of claim 1 further comprising an absorbent material coupled to the vaginal insert device.

6. An apparatus comprising:
   the vaginal insert, device of claim 1; and
   an applicator coupled to the vaginal insert device for facilitating insertion of the vaginal insert device.

7. A kit comprising:
   at least a first vaginal insert device as described in claim 1 and a second vaginal insert device as described in claim 1;
   wherein the first vaginal insert device comprises a first length and a first in-use diameter;
   wherein the second vaginal insert device comprises a second length and a second in-use diameter;
   wherein the second length is different from the first length, and the first in-use diameter is different from the second in-use diameter.

8. A vaginal insert device comprising:
   a compliable resilient material;
   a substantially conical support portion having a distal end and a proximal end, the support portion having a plurality of foldable areas extending from the distal end to the proximal end, the support portion having an insertion mode wherein a largest outer circumference of the support portion has an insertion diameter when the plurality of foldable areas are compressed; the support portion having an in-use mode wherein the largest outer circumference of the support portion has an in-use diameter larger than the insertion diameter, and the support portion having a removal mode;
   a stabilizing portion attached to the distal end of the support portion;
   at least one tubular fluid passageway surrounded by the compliable resilient material of the vaginal insert device and extending from the distal end to the proximal end of the support portion and open at the distal end and the proximal end of the support portion; and
   a removal member attached to the vaginal insert device.

9. The vaginal insert device of claim 8 wherein the insertion mode comprises the plurality of foldable areas compressed inward.

10. The vaginal insert device of claim 9 wherein the plurality of foldable areas expand to a maximum in-use diameter position to transition between the insertion mode and the in-use mode.

11. The vaginal insert device of claim 9 wherein the removal mode comprises the support portion in an elongated position wherein the largest outer circumference of the support portion has a removal diameter smaller than the in-use diameter.

12. The vaginal insert device of claim 11 wherein the removal member comprises a string; and
   tension on the string compels the support portion to an elongated position in transition between the in-use mode and the removal mode.

13. An apparatus comprising:
   the vaginal insert device of claim 8; and an applicator coupled to the vaginal insert device for facilitating insertion of the vaginal insert device.

14. The apparatus of claim 13 wherein the applicator maintains the support portion of the vaginal insert device in the insertion mode, and removal of the vaginal insert device from the applicator transitions the support portion from the insertion mode to the in-use mode.

* * * * *